United States Patent [19]
Christoudias

[11] Patent Number: 5,565,004
[45] Date of Patent: Oct. 15, 1996

[54] CHRISTOUDIAS TWIN FORCEPS APPROXIMATOR

[76] Inventor: George C. Christoudias, 17 Lower Cross Rd., Saddle River, N.J. 07548

[21] Appl. No.: 453,903

[22] Filed: May 30, 1995

[51] Int. Cl.$^6$ ..................................................... A61B 17/28
[52] U.S. Cl. ........................... 606/207; 606/205; 606/217; 81/487; 269/43
[58] Field of Search ..................................... 606/210, 211, 606/212, 205, 206, 207, 208, 209; 294/99.2; 128/321, 323, 325, 354

[56] References Cited

U.S. PATENT DOCUMENTS

| | | | |
|---|---|---|---|
| 2,214,984 | 9/1940 | Bachmann | 606/210 |
| 4,600,007 | 7/1986 | Lahodny et al. | 606/205 |
| 4,950,281 | 8/1990 | Kirsh et al. | 606/207 |

*Primary Examiner*—Michael Powell Buiz
*Assistant Examiner*—Kevin Truong

[57] ABSTRACT

The Christoudias twin forceps approximator comprises two moveable plates that are joined together at one end and a central plate of the same length which is also joined at the one end to the two metal plates or limbs. The two flexible metal plates close in a complimentary fashion against opposite sides of the central plate either simultaneously or sequentially with the thumb controlling one plate and the index finger the other, while the central plate is held steady with the palm and remaining fingers by means of a handle which is fastened to the central plate. Thus it is possible to approximate and affix tissues with a single instrument using only one hand. An alternate embodiment of the invention includes a stapler which is mounted to the forceps to fix the tissues once they are approximated by the twin forceps. Teeth on the inside surface of the free ends of the plates or jaws engage the tissue between the jaws of the forceps so that the tissue can be manipulated, rotated, etc. The device functions by sequentially grasping the tissues to be sutured to each other with a pair of forceps, approximating said tissues, and then sequentially passing a needle with an attached thread through such tissues or stapling said tissues.

3 Claims, 3 Drawing Sheets

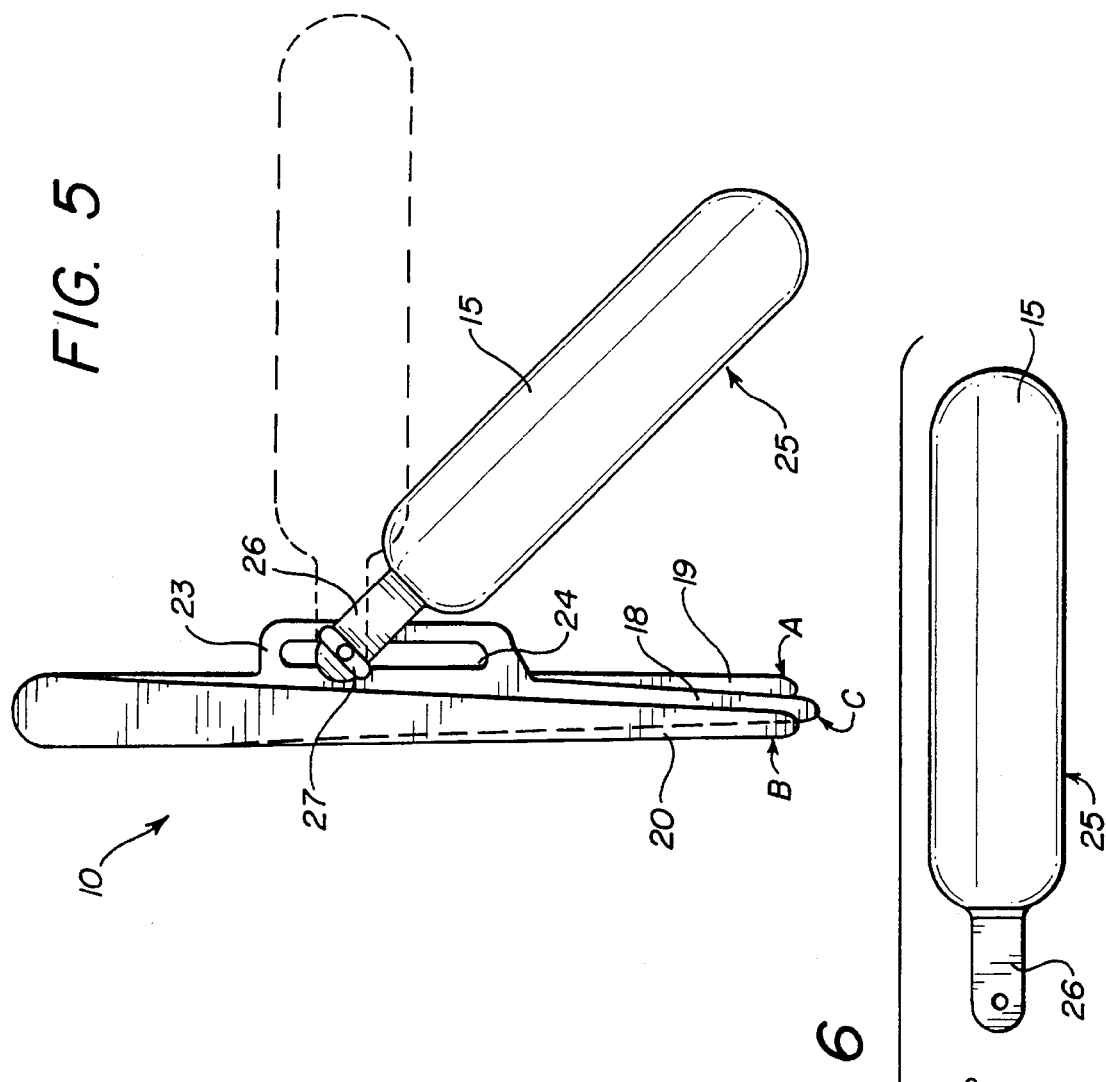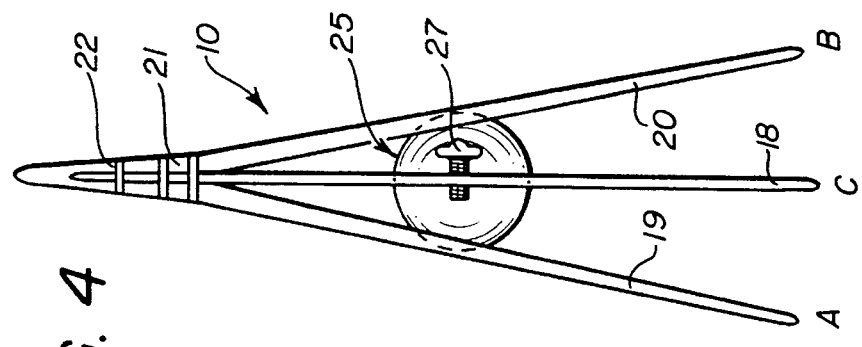

CHRISTOUDIAS TWIN FORCEPS APPROXIMATOR

BACKGROUND OF THE INVENTION

With the advent of laparoscopic surgery came a great need and stimulus for the development of new instrumentation. A considerable number of new instruments have been developed, introduced, and accepted over the past few years. The vast majority of these new surgical instruments, however, are specifically designed for the performance of laparoscopic surgical procedures and are seldom, if ever, suitable for conventional surgery.

In the prior art, all tissue forceps stem from a basic design comprised of two flexible metal plates, which are joined on one end. The two metal plates are spread apart beyond the affixed region due to the inherent spring like properties of these metal plates. The free ends or jaws of these plates are equidistant from the joined end and are brought to an apposition when the two plates are directed towards each other by squeezing them between the thumb on and the index finger.

The inside surfaces of the free ends or jaws of these plates are usually comprised of complimentary ridges and crevices, "teeth" and recesses, etc., so that, upon approximation, they hold firmly any tissue that is engaged between their two free ends or jaws. The configuration of the grasping surface, the presence or absence of teeth, and the size and smoothness of the jaws usually is connoted by the name of the forceps, such as Adson forceps, DeBakey forceps, intestinal forceps, forceps with teeth, plain forceps, "thin" forceps, packing forceps, etc.

Once the tissue is engaged between the jaws of the forceps, the tissue can be manipulated, rotated for inspecting the tissues, and/or approximated to another tissue. To a person familiar with the art of surgery, the forceps are commonly used to hold a tissue to be inspected, examined, or sutured to another tissue or organ. This is accomplished by sequentially grasping the tissues to be sutured to each other with a pair of forceps and then sequentially passing a needle with an attached thread through said tissues. An alternate method of suturing or stapling tissues to each other involves using two pairs of forceps, one with each hand, grasping two different parts of the tissues and bringing said parts of tissues together by approximating the forceps. The tissues can then be firmly affixed with a suture or a staple. This alternate method requires an assistant, who approximates the tissues and holds them while the surgeon inserts the needle to suture or fire the gun to staple the tissues together.

In laparoscopic procedures, an instrument, called the Maritsa tissue approximator, U.S. Pat. No. 5,403,332, is used to accomplish the tissue approximation but has a different mechanism of action and would be too cumbersome for use in conventional surgery.

The object of this invention is to accomplish the approximation of the tissues to be sutured or stapled or otherwise affixed together with one instrument using only one hand, the surgeon's. The other hand can be used for suturing or stapling the tissues together. In this manner, the need for an assistant is eliminated; the assistant can be used for exposure and retraction of the tissues, so that optimal visualization of the surgical field is established for the surgeon. In the performance of small procedures, when an assistant is not present, the surgeon can perform approximation of the tissues more expeditiously and precisely, thus achieving better results.

SUMMARY OF THE INVENTION

The Christoudias twin forceps are comprised of two movable limbs or elongated metal plates that are joined together at one end much as any other pair of surgical forceps, with the distinct difference that there is a central plate of equal length which is also joined at one end between the two metal plates or limbs. This central plate has also a free end onto which the other two metal plates or limbs close in a complimentary fashion on the opposing surfaces of the central plate. The closure of the movable plates against the central plate can be done simultaneously or sequentially with the thumb for the one and the index finger for the other, while the central plate is held steady with the palm of the hand and remaining fingers via a handle, which is securely fastened onto the central plate. The ends of the metal plates comprise grasping jaws with the central plate, including teeth or serrations on their interior. In one embodiment, the Christoudias twin forceps includes a stapler mounted thereto so that the approximation of tissues and the stapling may be accomplished by a single individual in rapid sequential steps.

Accordingly, a main object of this invention is to provide a new and improved method and instrument that permits one to single-handedly approximate two tissues in conventional surgery in preparation for affixing them with a suture or a staple without the need of an assistant.

A second object of this invention is to more expeditiously and precisely assist in approximating tissues in preparation for suturing or stapling in procedures when an assistant is usually not present.

A third object of this invention is to allow a surgeon to approximate and staple the tissues with only one instrument used by one hand by mounting the Christoudias twin forceps on a staple gun, which effectively becomes the handle of the twin forceps.

A more specific object of this invention is to provide a new and improved method of approximating tissues to be affixed with a suture or staple with one instrument using only one hand, said instrument comprising twin forceps having a central plate with approximating limbs on each side thereof.

BRIEF DESCRIPTION OF THE DRAWINGS

The above and other objects and advantages of the current invention are more clearly shown when viewed in conjunction with the accompanying drawings wherein:

FIG. 4 is a front view of the invention with the two movable lateral plates or limbs and a central plate onto which the lateral plates will close. The handle and retention screw of the central plate are also illustrated;

FIG. 5 is a perspective view of the invention with a clear view of the handle and the attaching mechanism engaging the central plate, allowing adjustments of the handle position with reference to the central plate.

FIG. 6 shows a side view of the handle with the handle retention mounted plate and a central aperture through which the retention screw is mounted for attaching and adjusting the handle onto the forceps via the retention plate and aperture.

DETAILED DESCRIPTION OF THE INVENTION

Figure 1:
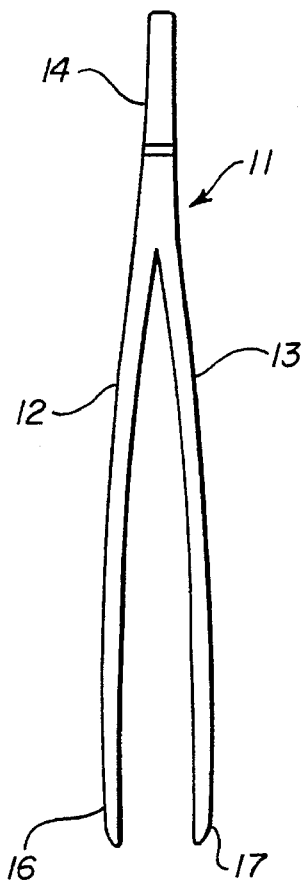
FIG. 1 is a front view of the standard pair of forceps of the prior art.

Referring now to the drawings the invention comprises an approximator known as the Christoudias twin forceps approximator 10. FIG. 1 depicts a prior art approximator 11 wherein the approximator limbs 12 and 13 are joined at an upper portion 14 which extends outwardly for a predetermined distance to facilitate manipulation of the forceps or approximator 11. The limbs 12 and 13 are flexible with the end points 16 and 17 used to grasp tissue when pressure is applied to the limbs 12, 13. Normally the two limbs or plates 12 and 13 are brought together by squeezing them between the thumb on one hand and the index finger on the other.

FIG. 4 illustrates the Christoudias twin forceps approximator 10 which comprises the present invention. The approximator 10 includes a central plate 18 and two plates 19 and 20 which are positioned equally distant on opposite sides of the central plate 18. The plates 19 and 20 are joined at a junction portion 21 together with the central plate 18. In one embodiment, the plates 19 and 20 comprise a unitary member with the central plate 18 being mounted therebetween by coupling members 22. The central plate 18 also includes a forceps retention plate 23 which extends rearwardly from the central plate 18 and includes an elongated retention slot 24 in which a handle 25 is mounted. The handle 25 as shown in FIGS. 5–6 comprises an elongated cylindrical member 15 with a handle retention plate 26 projecting outwardly at one end. The handle retention plate 26 includes an aperture 23 which engages a threaded retention screw 27. The movement of the handle 25 is shown in phantom in FIG. 5 and said handle 25 can be adjusted within the slot 24 at the operator's determination.

Figure 2:
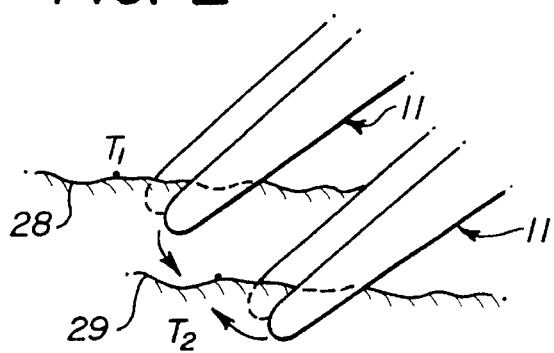
FIG. 2 shows the jaws of two pairs of forceps grasping two tissues to be approximated at two points; T1 and T2.
Figure 3:
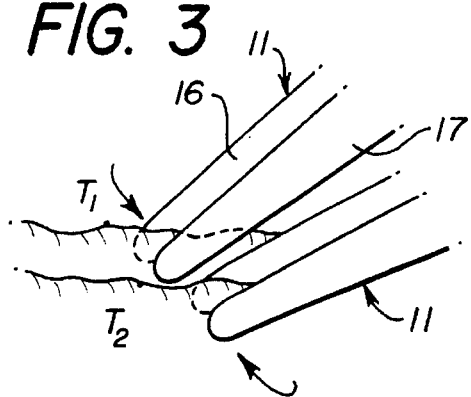
FIG. 3 shows the two points, T1 and T2, brought together by the approximating the tissues with the forceps prior to affixing the tissues with a stitch or a staple.

FIG. 2 depicts the operation of the prior art approximator 11 of FIG. 1 wherein, two forceps or approximators 11 are required to grasp the tissue 28 and 29 and approximate them together. Points T1 and T2 are brought together or approximated as shown in FIG. 3. This requires the use of two hands or two individuals. FIG. 3 is a further extension of the operation depicted in FIG. 2 with the tissues 28 and 29 brought together.

Figure 7:
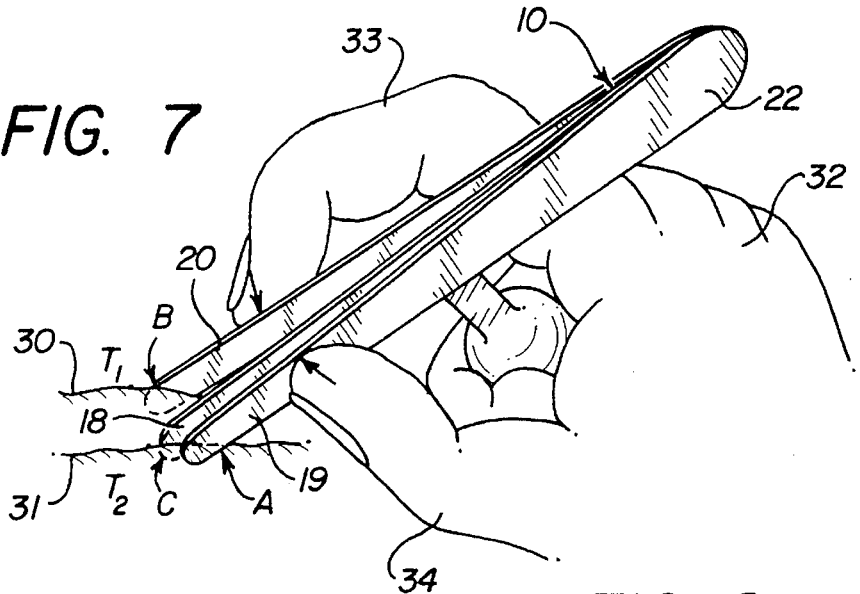
FIG. 7 shows the Christoudias twin forceps approximator in use with the central plate stabilized with the handle. The lateral plate is pressed onto the central plate, engaging the tissue at point T2. The other lateral plate is about to engage and move point T1 of the tissue onto the central plate, thus effectively approximating point T1 to T2.
Figure 8:
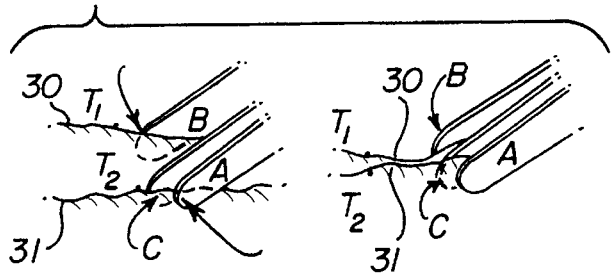
FIG. 8 shows points T1 and T2 on tissues as they are being engaged between the central plate and lateral plates and approximated.
Figure 9:
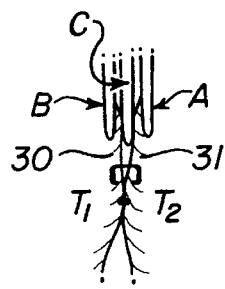
FIG. 9 shows a front view of the invention with the tissues approximated at points T1 and T2 and a staple affixing said tissues in place.

FIG. 7 depicts the operation of the Christoudias twin forceps approximator 10 wherein the tissues 30 and 31 are brought together with a single instrument 10 operated by one hand 32. The plate 19 is shown pressing the tissue 31 against the central plate 18 while plate 20 is being moved against tissue 30 to approximate it with tissue 31. The index finger 33 and thumb 34 are used to manipulate the approximator 10 with the upper junction portion 22 resting against the hand 32. FIG. 8 depicts the engagement of tissues 30 and 31 by the approximator 10. The movement of the respective limbs 19 and 20 is shown by the arrows. FIG. 9 shows the tissues 30 and 31 approximated and a staple 35 affixing the tissues 30 and 31 in place.

Figure 10:
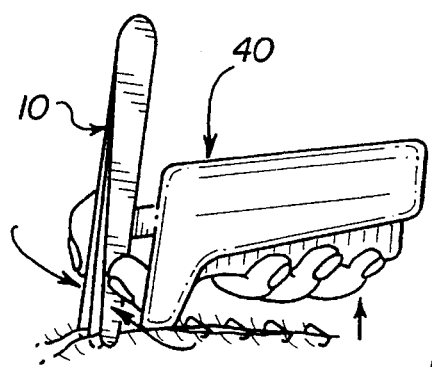
FIG. 10 is a side view of an alternate embodiment of the invention wherein the handle is replaced with a stapler gun, which is similarly mounted in an adjustable manner onto the twin forceps. Once the tissues are approximated by the twin forceps, the stapler gun can be fired with the same hand to apply the staple and affix the tissues; and, FIG. 10A shows the tissues being approximated and the staple gun being fired.
Figure 10A:
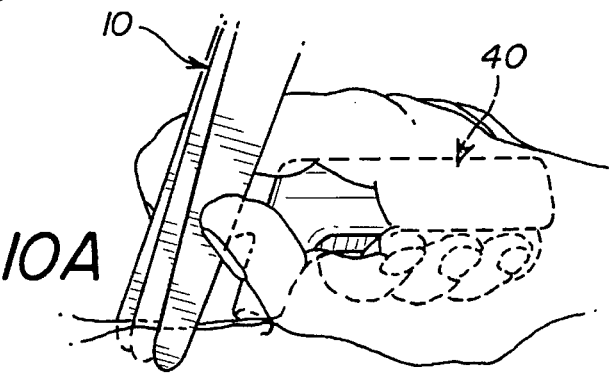

FIGS. 10–10a depict a staple gun 40 which comprises part of the apparatus 10 in an alternate embodiment. The stapler 40 extends rearwardly from the forceps 10 and can be used by one operator using one hand. The tissues 30, 21 are stapled together by the stapler 40, which replaces the handle 25, in a single rapid pass. This arrangement greatly facilitates and speeds up the operation. Furthermore, the forceps or approximator 10 can be used both in laparoscopic and conventional surgery.

While the invention has been explained by a detailed description of certain specific embodiments, it is understood that various modifications and substitutions can be made in any of them within the scope of the appended claims which are intended also to include equivalents of such embodiments.

What is claimed is:

1. The Christoudias hand-held forceps approximator for tissue comprising:

an upper junction portion, a central plate extending outwardly from the junction portion including a forceps retention plate extending rearwardly therefrom, said retention plate having a retention slot including a handle mounted thereto to assist in stabilizing and holding the approximator with the handle held in the palm of the hand, a first plate and a second plate extending outwardly from the junction portion on opposite sides and at an angle to the central plate wherein said first and second plates each cooperate with the central plate to approximate tissue together, said first plate being manipulated by the thumb on the one side of the central plate and the second plate being manipulated by the index or index and middle finger on the other side of the central plate with the approximator being stabilized by the handle held firmly in the palm of the hand.

2. An approximator in accordance with claim 1 wherein:

the handle comprises an elongated member having a handle retention plate extending outwardly therefrom and having an aperture therein and mounting means engaging said aperture and the retention slot in the forceps retention plate to mount the handle in a predetermined adjustable position.

3. The method of approximating tissues comprising:

providing a twin forceps approximator having a stable central plate stabilized by a rearwardly extending handle, and movable plates on each side thereof;

stabilizing the central plate by firmly holding the handle in the palm of the hand;

manipulating the first plate with the thumb and directing it towards the central plate to engage a first part of the tissues to be approximated;

moving the approximator with the engaged tissue adjacent to a second part of tissues to be approximated;

manipulating the second movable plate with the index or index and middle finger and forcing it onto the central plate engaging the second part of the tissues in approximation to the first part of the tissues; and, suturing, stapling or fixing the approximated tissues together.

* * * * *